(12) United States Patent
Martinez et al.

(10) Patent No.: US 7,754,913 B2
(45) Date of Patent: Jul. 13, 2010

(54) SYNTHESIS OF ISOTOPICALLY LABELED ALPHA-KETO ACIDS AND ESTERS

(75) Inventors: Rodolfo Antonio Martinez, Santa Fe, NM (US); Mark Minton, Linville, VA (US); Frank Elbert Anderson, III, Germantown, MD (US); Erick Gabriel Ortiz, Rio Rancho, NM (US); Kenneth Edmund Tortolani, Mt. Airy, MD (US)

(73) Assignee: Cambridge Isotope Laboratories, Inc., Andover, MA (US)

( * ) Notice: Subject to any disclaimer, the term of this patent is extended or adjusted under 35 U.S.C. 154(b) by 0 days.

(21) Appl. No.: 11/827,652

(22) Filed: Jul. 11, 2007

(65) Prior Publication Data

US 2008/0161593 A1    Jul. 3, 2008

Related U.S. Application Data

(60) Provisional application No. 60/830,301, filed on Jul. 11, 2006, provisional application No. 60/851,706, filed on Oct. 13, 2006.

(51) Int. Cl.
*C07C 69/66* (2006.01)
(52) U.S. Cl. ...................................... 560/174
(58) Field of Classification Search ........................ None
See application file for complete search history.

(56) References Cited

U.S. PATENT DOCUMENTS

| 4,769,464 | A * | 9/1988 | Sajtos ...................... 546/314 |
|---|---|---|---|
| 6,753,446 | B1 | 6/2004 | Martinez et al. |
| 2006/0178534 | A1 | 8/2006 | Martinez et al. |
| 2007/0106085 | A1 | 5/2007 | Alvarez et al. |
| 2008/0171893 | A1 | 7/2008 | Martinez et al. |
| 2008/0177101 | A1 | 7/2008 | Martinez et al. |
| 2008/0177115 | A1 | 7/2008 | Martinez et al. |

FOREIGN PATENT DOCUMENTS

| EP | 1661880 | 5/2006 |
|---|---|---|
| JP | 2001-354620 | 12/2001 |
| JP | 2004010595 | 1/2004 |
| JP | 2005042041 | 2/2005 |
| WO | 2005010061 | 2/2005 |
| WO | WO 2006/038811 | 4/2006 |
| WO | 2006054903 | 5/2006 |

OTHER PUBLICATIONS

Greene, Protective Groups in Organic Synthesis, 1981, John Wiley & Sons, Inc., New York, pp. 171-172.*
Ishii, Hisachi; Chemical & Pharmaceutical Bulletin 1990; 38(8); 2118-26.
Yamamoto, Yoshinori; Journal of Organic Chemistry 1986; 51(6); 886-91.
Johansen et al, Journal of Labelled Compounds & Radiopharmaceuticals (2004); 47(2); 127-138.
Ishihra et al., Tetrahedron (2002); 58(41); 8179-8188, Elsevier Science Ltd.
Banks et al., Journal of Organic Chemistry (1977); 42(24); 3965-6.
Hon et al, Tetrahedron (2003); 59(4); 492-498, Elsevier Scence Ltd.
Das et al., Snlett (1), 59-60; (2000).
Kijima et al, Journal of Organic Chemistry; 53(8); 1719-22; (1988).
Burbaum et al, Bioorganic Chemistry; 17(3); 359-71; (1989).
International Search Report, PCT/US2007/016209.
Kien, My et al, Organiz Mass Spectrometry, The Collisionally Induced Dissociation of Allyl and 2-Propenyl Cation. A 13C-Labelling Study, 1987, 22, pp. 113-114.
Comet et al, Journal of The American Chemical Society, Allylic Ionization Versus Oxidative Addition Into Vinyl C-X Bonds by Pd With Polyfunctional Olefin Templates, 126, 16087-16092.
Rieke et al, Journal of The American Chemical Society, Activated Metals, IV. Preparation and Reactions of Highly Reactive Magnesium Metal, 1974, 96(6) pp. 1775-1781.
Winkler, et al., "Principles and Results of Stable Isotope," Isotopes Environ. Health Stud., vol. 31:161-190 (1995).
Yasuo, et al., computer generated English translation and abstract of JP 06-121822, published May 6, 1994.

* cited by examiner

*Primary Examiner*—Paul A Zucker
(74) *Attorney, Agent, or Firm*—Foley & Larnder LLP; Michel Morency; James F. Ewing

(57) ABSTRACT

Isotopically labeled alpha-keto acids and esters are disclosed herein. Also disclosed are methods of synthesizing isotopically labeled alpha-keto acids and esters.

3 Claims, No Drawings

SYNTHESIS OF ISOTOPICALLY LABELED ALPHA-KETO ACIDS AND ESTERS

CROSS-REFERENCE TO RELATED APPLICATIONS

This application claims the benefit of the filing date of U.S. Provisional Patent Application No. 60/830,301 filed Jul. 11, 2006 and U.S. Provisional Patent Application No. 60/851,706 filed on Oct. 13, 2006, the disclosures of which are hereby incorporated herein by reference.

BACKGROUND OF THE INVENTION

Pyruvic acid ($C_3H_4O_3$) has the chemical name 2-oxopropanoic acid, and has a molecular mass of 88.06 grams per mol.

Pyruvic acid is a colorless organic liquid formed as an intermediate in carbohydrate metabolism and as an end product in glycolysis. Pyruvic acid has a melting point ranging from about 11° C. to about 12° C. and is soluble in water.

In the laboratory, pyruvic acid may be prepared by heating a mixture of tartaric acid and potassium hydrogen sulfate, or by the hydrolysis of acetyl cyanide, formed by a reaction of acetyl chloride with potassium cyanide. Production under these conditions, however, leaves undesirable impurities, which can be toxic or harmful if not removed in entirety.

Pyruvic acid also occurs naturally as an intermediate product in carbohydrate and protein metabolism in the human body. Pyruvic acid is important in metabolism as it can be converted to carbohydrates via gluconeogenesis, to fatty acids or energy through acetyl-CoA (which is the main input for a series of reactions known as the Krebs cycle), to the amino acid alanine, and to ethanol.

In industry, pyruvic acid is used to produce its salts and esters (pyruvates) for the use as dietary supplements and as an effective means of weight loss. Pyruvic acid is also used for the synthesis of amino acids and used for biomedical research. Its derivatives are used in making food additives and flavoring agents.

Unfortunately, due to the highly reactive nature of pyruvic acid, storage of the molecule over extended periods of time is very difficult and undesirable.

U.S. Pat. No. 6,753,446 describes diethyl oxalate analogs useful for asymmetric labeling of synthetic compounds. The compounds have the general structure RO—C(O)C(O)—X United States Patent Publication No. 2007/0106085 describes intermediates useful in the preparation of [$^{13}C_{1-5}$] metacrylic acid.

United States Patent Publication No. 2006/0178534 describes labeled compounds useful for the preparation of labeled compounds, including pyruvic acid.

SUMMARY OF THE INVENTION

In accordance with one embodiment of the present invention there is provided a process of forming an isotopically labeled compound of Formula (IIIb)

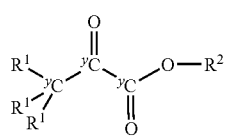

(Formula (IIIb))

comprising reacting a compound having Formula (IIIa)

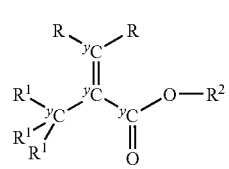

(Formula (IIIa))

with ozone in a solvent.

In accordance with another embodiment of this invention, $R^2$ is —$CH_2$—$R^4$, and $R^4$ is selected from the group consisting of phenyl, napthyl, benzofuran, isobenzofuran, indole, benzothiophenee, benzimidazole, indazole, benzoxazole, benzisoxazole, benzothiazole, pyridine, quinoline, isoquinoline, pyrazine, quinoxaline, pyridazine, cinnoline and the substituted variants thereof.

Recently, isotopically enriched pyruvic acid was studied for its use in a variety of medical diagnostic applications. The use of pyruvic acid that is isotopically enriched with at least one carbon 13 isotope allows for its use in medical diagnostics. Due to the highly reactive nature of pyruvic acid, storage of the molecule over extended periods of time is difficult and undesirable. Fortunately, storage of pyruvic acid is possible by forming shelf stable precursors of pyruvic acid, and then converting the precursor to pyruvic acid prior to its use, for example, as a medical diagnostic agent.

Disclosed are two synthetic pathways for the synthesis of precursors of pyruvic acid. The synthesis described herein provides pyruvic acid precursors of the present invention and derivatives in high yield which are shelf stable and which are of a high purity. Moreover, the pyruvic acid precursors allow conversion to pyruvic acid in one step. Finally, the synthetic methodologies of the present invention avoid the use of dangerous reagents, such as potassium cyanide.

DETAILED DESCRIPTION

The present invention provides compounds having Formula (I)

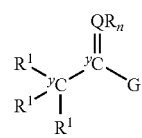

(Formula (I))

wherein:

G represents a halogen or a Grignard-halogen complex such as MgF, MgBr, MgCl, and MgI;

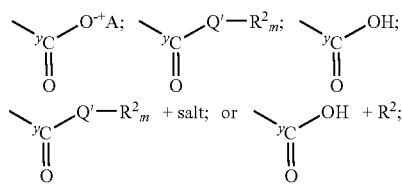

wherein $^+A$ represents a positively charged counterion;

Q represents C or O, each of which may be isotopically labeled;

Q' represents O or N, each of which may be isotopically labeled;

each R, each $R^1$, and each $R^2$ may be the same or different and independently may represent hydrogen, deuterium, tritium or a $C_1$-$C_{36}$ substituted or unsubstituted, saturated, or unsaturated, linear, branched, cyclic, aromatic, or substituted aromatic group, wherein R or $R^1$ may include a heteroatom including O, N, S, Si, and P wherein any of the carbon atoms or heteroatoms may be isotopically labeled;

m is 1 if Q' is O or 2 if Q' is N;

n is 0 if Q is O or 2 if Q is C; and y is independently 12, 13, or 14;

wherein the compound is not unlabeled pyruvic acid, the salts of pyruvic acid, unlabeled benzyl pyruvate, unlabeled benzyl methacrolate, propanoic-3-$^{13}C$ acid-2-oxo-phenylmethyl ester; or 2-propenoic acid-2-(methyl-$^{13}C$-d3)-phenylmethl ester.

As used herein, the terms "isotope", "isotopic" or "isotopically labeled" refer to an atom having the same number of protons but a different number of neutrons as compared with the most abundant form of the element. Accordingly, carbon may be isotopically labeled as $^{13}C$, nitrogen may be isotopically labeled as $^{15}N$, sulfur may be isotopically labeled as $^{32}S$ and oxygen may be isotopically labeled as $^{16}O$, $^{17}O$ or $^{18}O$. These terms as used herein also refer to radio-labeled elements. Further, these terms as used herein also refer to molecules which contain isotopic atoms.

The terms "aromatic" or "cyclic group" as used herein, encompasses not only the group but also the substitutions in one or more positions. Substitutions may include, and without limitation, halogens, hydroxyl, nitro, amino, substituted amino having the formula —$N(R^3)(R^3)$, (wherein $R^3$ is a $C_1$-$C_6$ linear, branched, or cyclic alkyl group), $C_1$-$C_5$ alkoxy, or $C_1$-$C_5$ alkyl groups. Thus, for example, a reference to a benzyl group can include, for example, meta-chloro benzene, 3,4,5 tri-bromo benzene, p,m,o-methyl, p,m,o-methoxy, and trifluoromethyl.

Hydrogen atoms, which by convention are not shown, may be deuterium or tritium.

In a preferred embodiment, at least one atom in Formula (I) is isotopic. More preferably, at least one carbon or $^yC$ is $C^{13}$ or $C^{14}$.

The present invention also provides compounds of Formula (II)

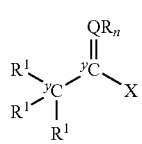

(Formula (II))

wherein:

X represents F, Cl, Br, I, MgF, MgCl, MgBr and MgI;

Q represents C which may be isotopically labeled;

each R, each $R^1$, and each $R^2$ may be the same or different and independently may represent hydrogen, deuterium, tritium or a $C_1$-$C_{36}$ substituted or unsubstituted, saturated, or unsaturated, linear, branched, cyclic, aromatic, or substituted aromatic group, wherein R or $R^1$ may include a heteroatom including O, N, S, Si, and P wherein any of the carbon atoms or heteroatoms may be isotopically labeled;

n is 2; and y is independently 12, 13, or 14.

In some embodiments, each R and each $R^1$ each may be the same or different and independently may be selected from hydrogen, deuterium, tritium or a $C_1$-$C_{24}$ substituted or unsubstituted, saturated or unsaturated, linear, branched, cyclic, aromatic or substituted aromatic moiety optionally containing one or more heteroatoms including O, N, S, P, and Si, any of which may be isotopically labeled.

In other embodiments, each R and each $R^1$ may be the same or different and independently may be selected from hydrogen, deuterium, tritium or a $C_1$-$C_{16}$ substituted or unsubstituted, saturated or unsaturated, linear, branched, cyclic, aromatic or substituted aromatic moiety optionally containing one or more heteroatoms including O, N, S, P, and Si, any of which may be isotopically labeled.

In yet other embodiments, each R and each $R^1$ may be the same or different and independently may be selected from hydrogen, deuterium, tritium or a $C_1$ to $C_6$ linear or branched, substituted or unsubstituted, cyclic, or aromatic moiety, optionally containing one or more heteroatoms including O, N, S, P, and Si, any of which may be isotopically labeled.

In preferred embodiments of the compositions of Formula (II), each R, each $R^1$, and each $R^2$ may be the same or different and independently may be selected from nitrogen, deuterium, methyl, ethyl, propyl, isopropyl, butyl, secbutyl, tertbuytl, allyl, 2-butenyl, 3-butenyl, phenyl, benzyl, napthyl, cyclopropyl, cyclopentyl, and cyclohexyl, thienyl, furyl, pyridyl, imidazoylyl, benzimidazoyl, or benzothiazolyl.

In a preferred embodiment, at least one atom in Formula (II) is isotopic. More preferably, at least one carbon is $^{13}C$ or $^{14}C$. Most preferably, at least one $^yC$ is $^{13}C$ or $^{14}C$.

In some embodiments, the compounds of Formula (II) have the structure of Formula (IIa):

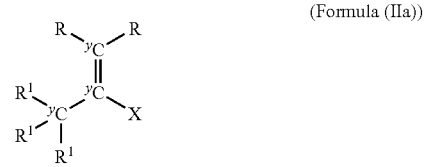

(Formula (IIa))

wherein R and $R^1$ are as defined previously.

In other embodiments, the compounds of Formula (II) have the structure of Formula (IIb):

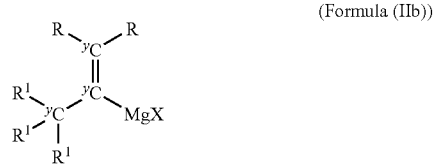

(Formula (IIb))

wherein R and $R^1$ are as defined previously.

Non-limiting examples of compounds falling within the scope of the compounds of Formula (II) include:

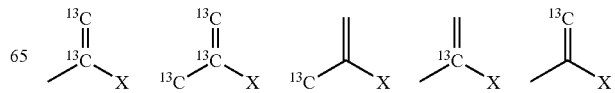

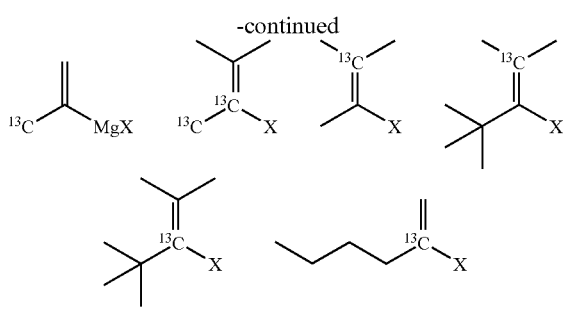

The present invention also provides compounds of Formula (III)

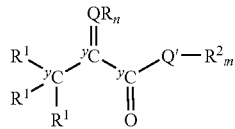

wherein:

Q represents C or O, each of which may be isotopically labeled;

Q' represents O, or N, each of which may be isotopically labeled;

each R, each $R^1$, and each $R^2$ may be the same or different and independently may represent hydrogen, deuterium, tritium or a $C_1$-$C_{36}$ substituted or unsubstituted, saturated, or unsaturated, linear, branched, cyclic, aromatic, or substituted aromatic group, wherein R or $R^1$ may include a heteroatom including O, N, and S, wherein any of the carbon atoms or heteroatoms may be isotopically labeled;

m is 1 or 2;

n is 0 or 2; and y is independently 12, 13, or 14;

wherein the compound is not unlabeled pyruvic acid, the salts of pyruvic acid, unlabeled benzyl pyruvate, unlabeled benzyl methacrolate, propanoic-3-$^{13}$C acid-2-oxo-phenylmethyl ester; or 2-propenoic acid-2-(methyl-$^{13}$C-d3)-phenylmethl ester.

In a preferred embodiment, at least one atom in Formula (III) is isotopic. More preferably, at least one carbon or $^yC$ is $C^{13}$ or $C^{14}$ In some embodiments, each R, each $R^1$, and each $R^2$ may be the same or different and independently may be selected from hydrogen, deuterium, tritium or a $C_1$-$C_{24}$ substituted or unsubstituted, saturated or unsaturated, linear, branched, cyclic, aromatic or substituted aromatic moiety optionally containing one or more heteroatoms including O, N, S, Si, and P any of which may be isotopically labeled.

In other embodiments, each R, each $R^1$, and each $R^2$ may be the same or different and independently may be selected from hydrogen, deuterium, tritium or a $C_1$-$C_{16}$ substituted or unsubstituted, saturated or unsaturated, linear, branched, cyclic, aromatic or substituted aromatic moiety optionally containing one or more heteroatoms including O, N, and S, any of which may be isotopically labeled.

In yet other embodiments, each R, each $R^1$, and each $R^2$ may be the same or different and independently may be selected from hydrogen, deuterium, methyl, ethyl, propyl, isopropyl, butyl, secbutyl, tertbuytl, allyl, 2-butenyl, 3-butenyl, phenyl, benzyl, napthyl, cyclopropyl, cyclopentyl, cyclohexyl, thienyl, furyl, pyridyl, imidazoylyl, benzimidazoyl, or benzothiazolyl.

In yet further embodiments, $R^2$ is selected from a protecting group including but not limited to methoxymethyl ether, tetrahydropyranyl ether, t-Butyl ether, allyl ether, benzyl ether, trimethylsilyl ethers, triethylsilyl ethers, t-butyldimethylsilyl ether, t-butyldiphenylsilyl ether, acetic acid ester, benzoic acid ester, methylthiomethyl ethers, benzyloxymethyl ethers, 2-napthylmethyl ethers, p-methoxybenzyl ethers, trityl ethers, and methoxytrityl ethers.

In some embodiments, Q is C; Q' is O; and $R^2$ is H, and at least one $^yC$ group is $^{13}C$ or $^{14}C$.

In other embodiments, Q is C; Q' is O; and $R^2$ is benzyl, and at least one $^yC$ group is $^{13}C$ or $^{14}C$.

In further embodiments, Q is O; Q' is O; and $R^2$ is benzyl, and at least one $^yC$ group is $^{13}C$ or $^{14}C$.

In yet other embodiments, the compounds of Formula (III) have the structure of Formula (IIIa):

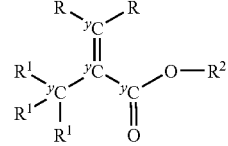

wherein $^yC$, R, $R^1$, and $R^2$ are as defined previously.

In yet further embodiments, the compounds of Formula (III) have the structure of Formula (IIIb):

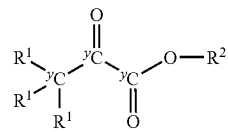

wherein $^yC$, R, $R^1$, and $R^2$ are as defined previously.

In preferred embodiments, the compounds of Formula (III) have the structure of Formula (IIIc)

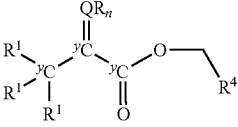

wherein:

Q, $^yC$, R, and $R^1$ are as defined previously; and $R^4$ represents a $C_1$-$C_{10}$ aromatic ring optionally substituted with one or more nitro, amino, substituted amino having the formula —N($R^3$)($R^3$), halogen, deuterium, tritium, $C_1$-$C_4$ alkoxy, or $C_1$-$C_4$ alkyl groups, wherein the aromatic ring optionally includes a heteroatom selected from the group consisting of O, N, and S.

Examples of aromatic rings representative of $R^4$ include, but are not limited to, phenyl, napthyl, benzofuran, isobenzofuran, indole, benzothiophenee, benzimidazole, indazole, benzoxazole, benzisoxazole, benzothiazole, pyridine, quinoline, isoquinoline, pyrazine, quinoxaline, pyridazine, cinnoline and the substituted variants thereof.

It has been found that the inclusion of a single carbon spacer adjacent to $R^4$, as in Formula (IIIc) and the Formulas which follow, allows for cleavage of the $R^2$ group (Formula (III)) by means of hydrogenation rather than acid hydrolysis. As discussed herein, hydrogenation provides an efficient means by which the compounds of Formula (IIIc) can eventually be converted to pyruvic acid or its derivatives thereof. Moreover, hydrogenation allows for the production of pyruvic acid under neutral conditions and where the only byproduct is toluene. Other methods, including acid hydrolysis, leave inorganic or organic acids as impurities.

In more preferred embodiments, the compounds of Formula (III) have the structure of Formula (IIId):

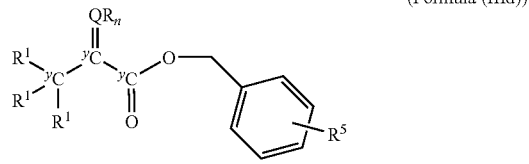

(Formula (IIId))

wherein Q, $^y$C, R, and $R^1$ each are as defined previously; and $R^5$ represents at most 5 substitutions on the aromatic ring, wherein $R^5$ independently represents nitro, amino, substituted amino having the formula —N($R^3$)($R^3$), halogen, deuterium, tritium, $C_1$-$C_4$ alkoxy, or $C_1$-$C_4$ alkyl group.

In one particularly preferred embodiment, the compounds of Formula (IIId) have the structure of Formula (IIIe):

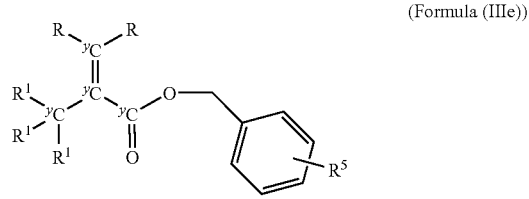

(Formula (IIIe))

wherein $^y$C, R, $R^1$, and $R^5$ are as defined previously.

In another particularly preferred embodiment, the compounds of Formula (IIId) have the structure of Formula (IIIf):

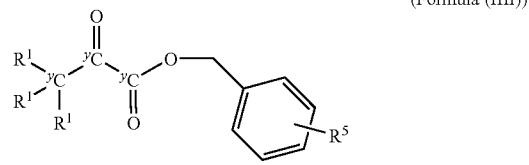

(Formula (IIIf))

wherein $^y$C, $R^1$, and $R^5$ are as defined previously.

In another particularly preferred embodiment, the compounds of Formula (IIIe) have the structure of Formula (IIIg):

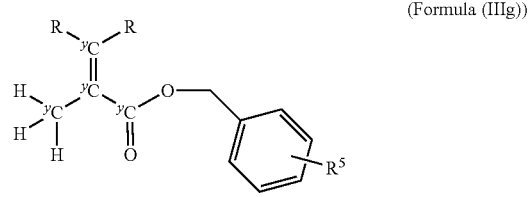

(Formula (IIIg))

wherein $^y$C, R, and $R^5$ are as defined previously.

In another particularly preferred embodiment, the compounds of Formula (IIIe) have the structure of Formula (IIIh):

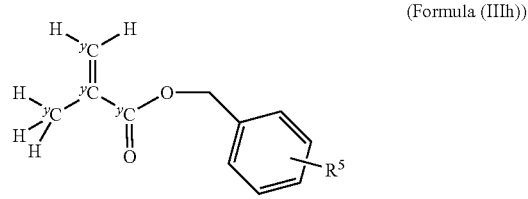

(Formula (IIIh))

wherein $^y$C and $R^5$ are as defined previously.

In yet another particularly preferred embodiment, the compounds of Formula (IIIf) have the structure of Formula (IIIi):

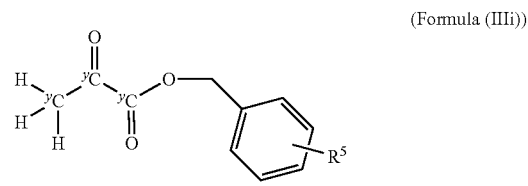

(Formula (IIIi))

wherein $^y$C and $R^5$ are as defined previously.

In a most preferred embodiment of Formula (IIIi), each $R^5$ is hydrogen.

In yet another particularly preferred embodiment, the compounds of Formula (IIId) have the structure of Formula (IIIj):

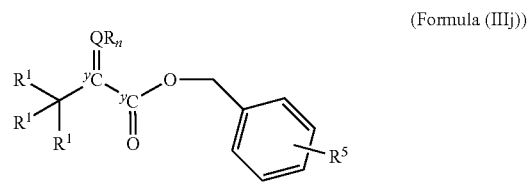

(Formula (IIIj))

wherein $^y$C, Q, n, R, $R^1$, and $R^5$ are as defined previously.

As illustrated below in Formula (IIIj), in a preferred embodiment in accordance with the present invention and particularly for those isotopically labeled compounds discussed herein having the structures generally shown in Formulas IIIa through IIIi, as well as Formula V, it is preferred that the double bond oxygen on the ester forming carbonyl, the carbon of the ester forming carbonyl and/or the carbon of the methacrylate or ketone group be isotopically labeled. In a particularly preferred embodiment in accordance with the present invention, the isotopic labeling of the compounds described above would occur at some atom other than the carbon bound to the various $R^1$ groups. Isotopically labeling may occur at a plurality of other groups as well.

Non-limiting examples of the compounds of Formulas (IIIe) and Formula (IIIf) include:

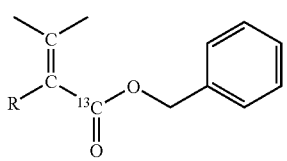

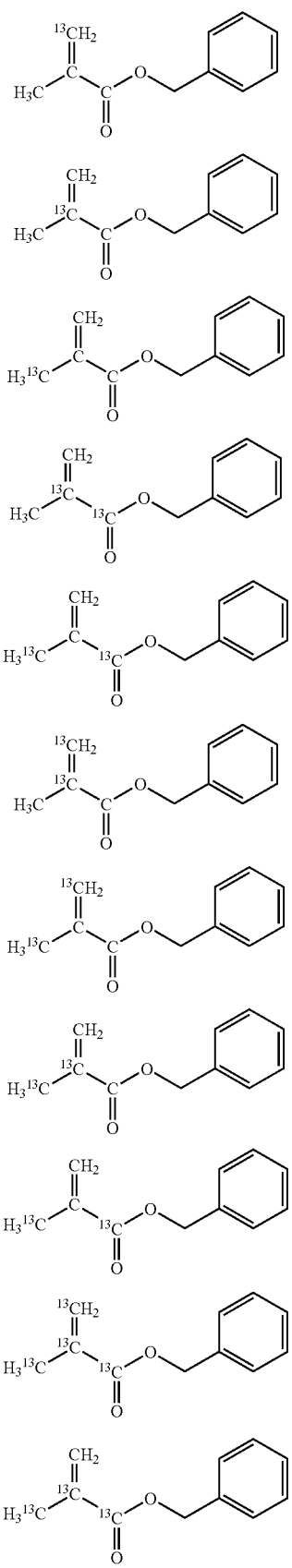
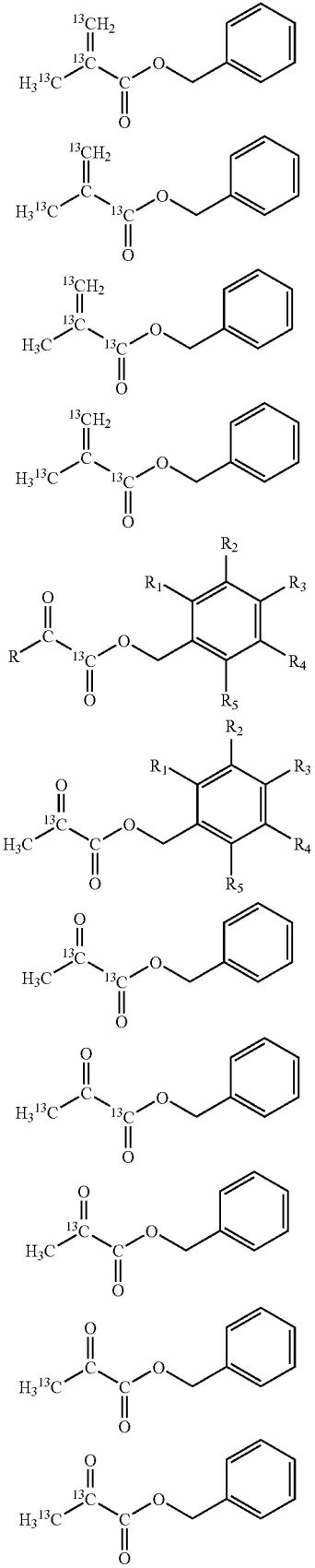

-continued

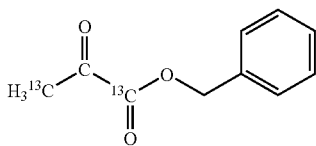

In other embodiments, the compounds of Formula (I) have the structure of Formula (IV):

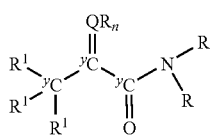

(Formula (IV))

wherein $^yC$, Q, R, and $R^1$ are as defined previously.

Non-limiting examples of the compounds of Formulas (IV) include:

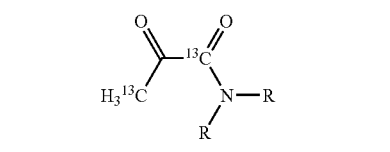

[1,3-$^{13}C_2$]Propanamide, N,N-dialkyl-2-oxo-

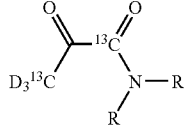

[1,3-$^{13}C_2$, 3,3,3-$d_3$]Propanamide, N,N-dialkyl-2-oxo-

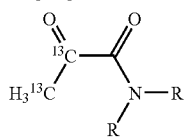

[2,3-$^{13}C_2$]Propanamide, N,N-dialkyl-2-oxo-

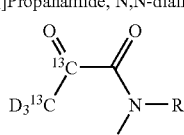

[2,3-$^{13}C_2$, 3,3,3-$d_3$]Propanamide, N,N-dialkyl-2-oxo-

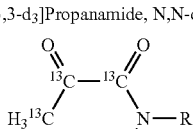

[1,2,3-$^{13}C_3$]Propanamide, N,N-dialkyl-2-oxo-

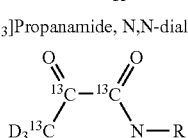

[1,2,3-$^{13}C_3$, 3,3,3-$d_3$]Propanamide, N,N-dialkyl-2-oxo-

-continued

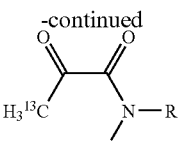

[3-$^{13}C$]Propanamide, N,N-dialkyl-2-oxo-

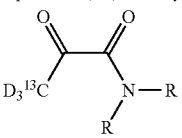

[3-$^{13}C$, 3,3,3-$d_3$]Propanamide, N,N-dialkyl-2-oxowherein R represents $R^2$ of Formula (IV).

In the propamides of Formula (IV) above, R is preferably a $C_1$-$C_4$ alkyl, more preferably methyl or ethyl.

The present invention also provides a method of synthesizing isotopically labeled compounds including analogs of pyruvic acid.

One synthetic method, according to the following scheme, comprises reacting a compound of Formula (IIa) with magnesium turnings in a solvent to yield a compound having Formula (IIb):

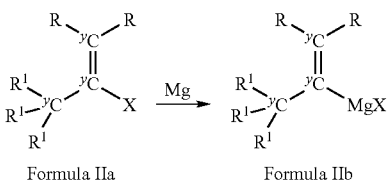

Formula IIa      Formula IIb

Preferably, the solvent is an aprotic solvent. More preferably, the solvent is an ether or toluene.

Preferably, the reaction is run at room temperature, more preferably the reaction is initially run at room temperature with a subsequent increase in temperature to drive the reaction to completion. As used herein, "room temperature" means a temperature ranging from about 22° C. to about 26° C.

In a preferred embodiment, each R and each $R^1$ may be the same or different and independently may be selected from hydrogen or $C_1$-$C_4$ alkyl, more preferably each R and each $R^1$ are hydrogen.

Another synthetic method, according to the following scheme, comprises reacting a compound of Formula (IIb)) with labeled or unlabeled carbon dioxide in a solvent to yield a compound having Formula (IIIa'):

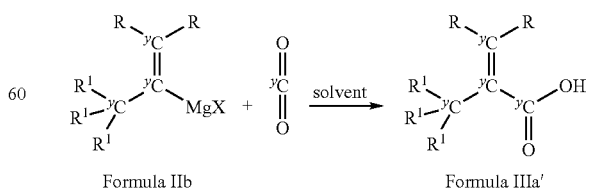

Formula IIb      Formula IIIa'

Preferably, the solvent is selected from ether, tetrahydrofuran, dioxane, and glymes.

Preferably, the reaction is run with cooling, more preferably at a temperature of about 0° C. or below, most preferably at about –50° C. or below.

In a preferred embodiment, each R and each $R^1$ may be the same or different and independently may be selected from hydrogen and $C_1$-$C_4$ alkyl, more preferably each R and each $R^1$ are hydrogen.

Another synthetic method, according to the following scheme, comprises reacting a compound of Formula (IIIa') with a weak base in the presence of a reagent having a halogenated leaving group to yield a compound having Formula (IIIb):

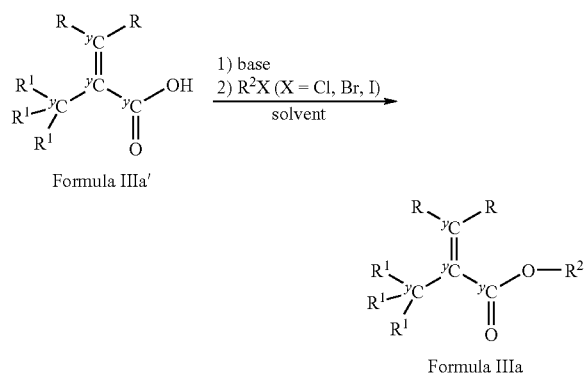

Formula IIIa'

Formula IIIa

Preferably, bases include $K_2CO_3$, $NaHCO_3$, $Li_2CO_3$, $Cs_2CO_3$, t-ButOK, t-ButOLi, hydroxides, alkyl salts, lithium salts, metal hydrides, and heteroatom bases. More preferably the base is $K_2CO_3$.

In a preferred embodiment, $R^2X$ is benzyl chloride or benzyl bromide.

In a preferred embodiment, the reaction is run at room temperature or below. One skilled in the art would recognize that the reaction may be run at temperatures lower than room temperature (between room temperature and –78° C.) to accommodate certain bases.

In a preferred embodiment, each R and each $R^1$ may be the same or different and independently may be selected from hydrogen and $C_1$-$C_4$ alkyl, more preferably each R and each $R^1$ are hydrogen.

In a preferred embodiment $R^2$ is —$CH_2$—$R^4$, wherein $R^4$ includes, but is not limited to, phenyl, napthyl, benzofuran, isobenzofuran, indole, benzothiophenee, benzimidazole, indazole, benzoxazole, benzisoxazole, benzothiazole, pyridine, quinoline, isoquinoline, pyrazine, quinoxaline, pyridazine, cinnoline and the substituted variants thereof.

Yet another synthetic method, according to the following scheme, comprises reacting a compound for Formula (IIIa) with ozone in a solvent to yield a compound having Formula (IIIb):

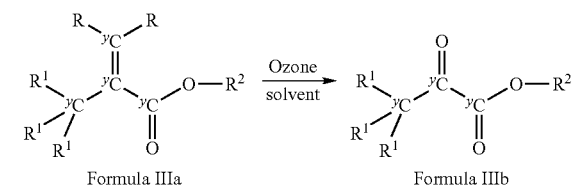

Formula IIIa

Formula IIIb

Preferably, this reaction is run in a $C_1$-$C_6$ alcohol (straight chain or branched), methylene chloride, chloroform and the like.

Preferably, the reaction is run at a reduced temperature, more preferably at about 0° C. or below. As used herein, the term "reduced temperature" refers to a temperature below room temperature.

In a preferred embodiment, each R and each $R^1$ may be the same or different and independently may be selected from hydrogen and $C_1$-$C_4$ alkyl, more preferably each R and each $R^1$ are hydrogen.

In a preferred embodiment $R^2$ is —$CH_2$—$R^4$, wherein $R^4$ includes but is not limited to, phenyl, napthyl, benzofuran, isobenzofuran, indole, benzothiophenee, benzimidazole, indazole, benzoxazole, benzisoxazole, benzothiazole, pyridine, quinoline, isoquinoline, pyrazine, quinoxaline, pyridazine, cinnoline and the substituted variants thereof. In a more preferred embodiment, $R^2$ is benzyl.

Yet a further synthetic method, according to the following scheme, comprises converting a compound having Formula (IIIb) to isotopically labeled pyruvic acid or an analog thereof by means of hydrogenation, preferably in a solvent selected from a $C_1$-$C_6$ alcohol (straight chain or branched), a ketone, water, an ether, or mixtures thereof.

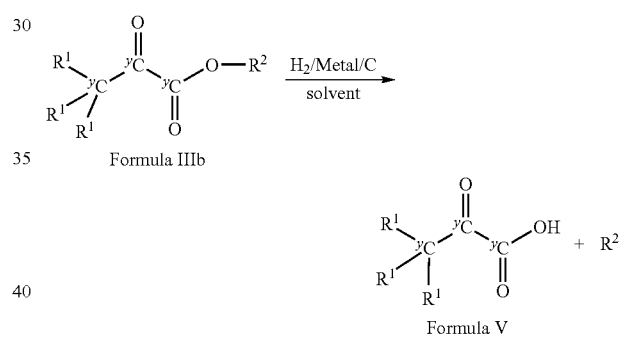

Formula IIIb

Formula V

The reaction is preferably run under a pressure of about 4 to about 12 psig, more preferably the reaction is run using a palladium catalyst, even more preferably the palladium catalyst is on charcoal.

The reaction is preferably run at room temperature.

In a preferred embodiment, each $R^1$ is independently selected from hydrogen or $C_1$-$C_4$ alkyl, more preferably each $R^1$ is hydrogen.

The above conversion can also be carried out via acid hydrolysis using techniques known to those of skill in the art. United States Patent Publication No. 2006/0178534, incorporated herein by reference, describes a method of performing acid hydrolysis. For example, acid hydrolysis may be accomplished by treating a compound with 1M HCl and then extracting the final product with an organic solvent, preferably ethyl acetate.

Yet a further synthetic method, according to the following scheme, comprises converting a compound having Formula (IIIf) to isotopically labeled pyruvic acid or an analog thereof by means of hydrogenation, preferably in a solvent selected from a $C_1$-$C_6$ alcohol (straight chain or branched), a ketone, water, an ether, or mixtures thereof.

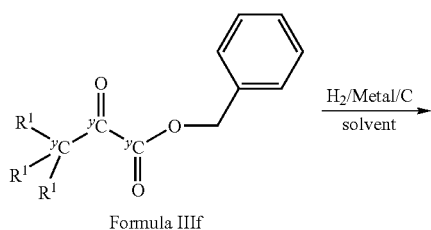

Formula IIIf

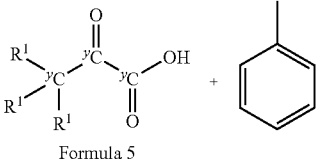

Formula 5

The reaction is preferably run under a pressure of about 4 to about 12 psig, more preferably run using a palladium catalyst, even more preferably the palladium is on charcoal.

In a preferred embodiment, each $R^1$ is independently selected from hydrogen or $C_1$-$C_4$ alkyl, more preferably each $R^1$ is hydrogen.

Yet a further synthetic method, according to the following scheme, comprises converting a pyruvate salt or an analog thereof to the respective pyruvate analog of Formula (IIIb) as follows:

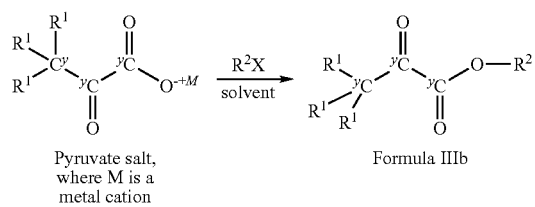

Pyruvate salt, where M is a metal cation

Formula IIIb

Preferably, the solvent is a polar aprotic solvent. More preferably, the solvent is dimethylformamide.

In a preferred embodiment, each $R^1$ is independently selected from hydrogen or $C_1$-$C_4$ alkyl, more preferably each $R^1$ is hydrogen.

Preferably $R^2X$ is $R^2Br$. More preferably, $R^2X$ is benzyl bromide.

This method of converting an isotopically labeled pyruvate salt to the respective pyruvate analog is particularly useful in isolating or purifying pyruvate salts from materials which contain dimerized pyruvic acid.

The compounds of Formula (IIIb), formed occurring to the reaction, are separated by techniques known in the art, preferably by distillation or chromatography.

The compounds of Formula (IIIa) synthesized by this process can then be converted to the respective isotopically labeled pyruvic acid analogs as described previously or even converted to the same pyruvate salt (but having a higher purity than the original pyruvate salt).

Accordingly, one synthetic route to pyruvic acid or the intermediates of pyruvic acid using the compounds generally described in Formulas (I), (II), and (III) is as follows:

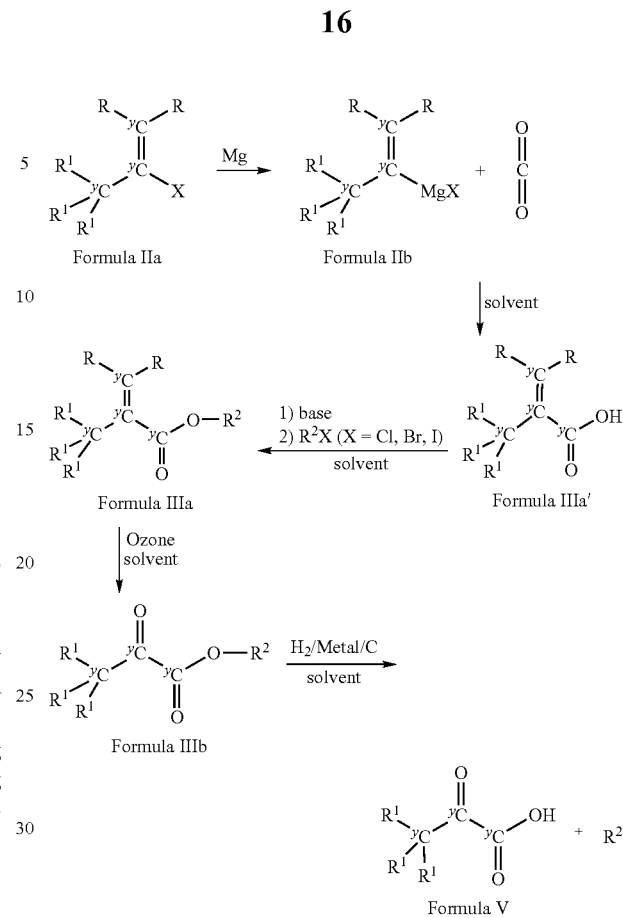

In general, magnesium turnings are combined with Formula IIa to yield the Gringard reagent Formula IIb. Formula IIb is then reacted in the presence of isotopically labeled carbon dioxide (wherein the oxygen atoms may optionally be isotopically labeled) to yield the intermediate of Formula IIIa'. This reaction can be run in an organic solvent selected from ether and related solvents including tetrahydrofuran, dioxane, glymes and the like.

The reaction is preferably run with cooling and more preferably at a temperature of about 0° C. or below, more preferably about −50° C. or below. The reaction is also preferably run in an inert atmosphere.

Intermediate Formula IIIa' is then reacted with a weak base in a solvent including methylene chloride, THF, or acetone at room temperature or above and with a reagent having a halogenated leaving group to arrive at the compound of Formula IIIa. One of ordinary skill in the art would be able to determine the necessary reagent having a halogenated leaving to arrive at the desired pyruvate derivative. For example, the reagent having a halogenated leaving group may be selected from benzyl chloride. Bases useful in the processes of the present invention include $K_2CO_3$, $NaHCO_3$, $Li_2CO_3$, $Cs_2CO_3$, t-ButOK, t-ButOLi, hydroxides, metal hydrides, and alkyl salts.

Ozonolysis is then carried out in the presence of Formula IIIa to yield the compound of Formula IIIb. Preferably, this reaction can be run in a $C_1$-$C_6$ alcohol (straight chain or branched), methylene chloride, chloroform and the like at a reduced temperature, more preferably at about 0° C. or below.

Finally, the compound of Formula IIIb is hydrogenated to yield the isotopically labeled pyruvic acid of Formula V. This can be run in a $C_1$-$C_6$ alcohol (straight chain or branched), a ketone, water, an ether, or mixtures thereof. The reaction is preferably run under a pressure of about 4 to about 12 psig, more preferably run using a palladium catalyst, even more preferably on charcoal. The hydrogenation could also be run in acetone.

This step could also be undertaken using by means of acid hydrolysis under conditions known to those of skill in the art.

Although the scheme shown above is one method of producing pyruvic acid, one of skill in the art would understand that any of the intermediates described above can be synthesized, isolated, and recovered independently of one another. The intermediates may be used to produce pyruvic acid intermediates or other compounds not disclosed herein.

Isotopically labeled pyruvic acid analogs can also be prepared by hydrolyzing compounds having Formula (IV) under acidic conditions. By means of example, the production of [1-$^{13}$C]pyruvic acid by means of acid hydrolysis is illustrated below.

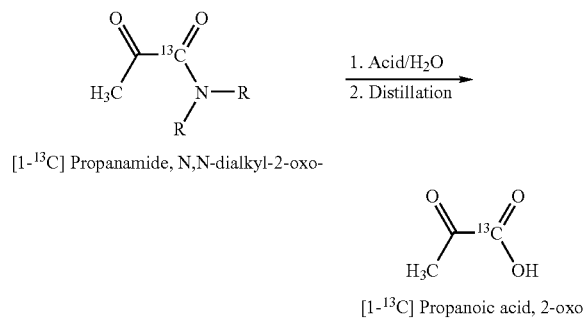

Compounds having Formula (IV) can be produced from isotopically labeled N,N-dialkyl-2-oxo-oxamates by Grignard addition, as follows:

Synthesis of [1-$^{13}$C]Propanamide, N,N-dialkyl-2-Oxo

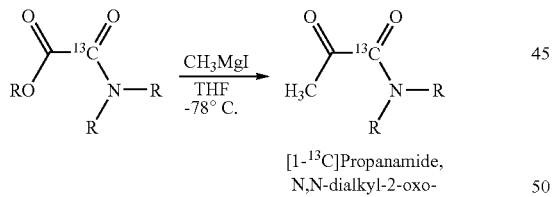

wherein R is as defined as $R^2$ in Formula (IV).

Synthesis of [2-$^{13}$C]Propanamide, N,N-dialkyl-2-Oxo

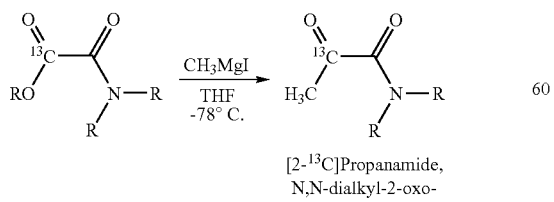

wherein R is as defined as $R^2$ in Formula (IV).

Synthesis of [1,2-$^{13}$C$_2$]Propanamide, N,N-dialkyl-2-Oxo

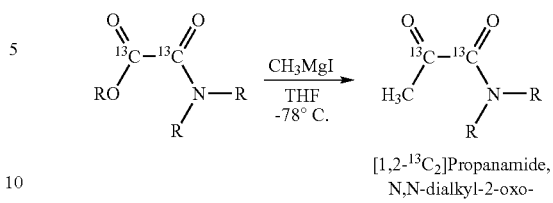

wherein R is as defined as $R^2$ in Formula (IV).

Starting materials for the above conversion to compounds having Formula (IV) may be produced in accordance with U.S. Pat. No. 6,753,446, incorporated herein by reference. For example, an oxamide may be prepared according to the following: [$^{13}$C]Methyl phenyl sulfide was reacted with sec-butyl lithium followed by [$^{13}$C]carbon dioxide to form intermediate (I). This intermediate (I) was then reacted with oxalyl chloride followed by dimethyl amine to form intermediate (II). This intermediate (II) was then reacted with sulfuryl chloride followed by 10 percent water in ethanol to form [1-$^{13}$C]acetic acid, (dimethylamino)oxo-, ethyl ester.

Compounds of Formula (IV) can also be prepared by reacting compounds having Formula (IIIa') with oxalyl chloride to form an acid halide intermediate, followed by reaction with an amine to form the di-substituted amide having Formula (IV). For example, the reaction with oxalyl chloride, and amine, proceeds as follows:

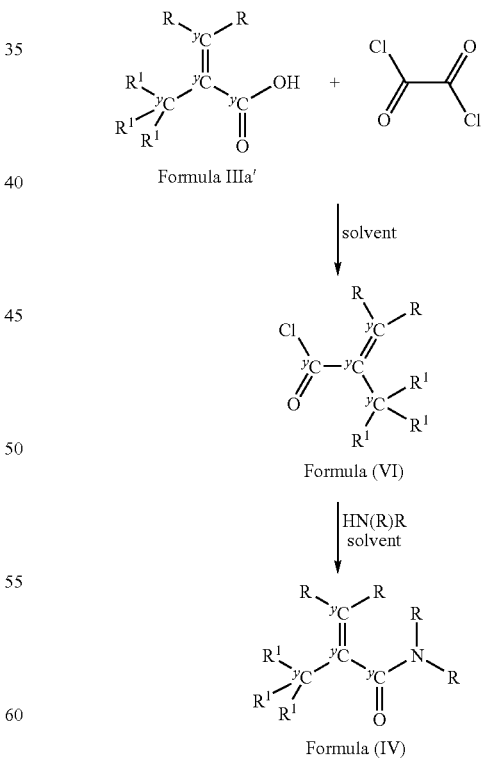

Preferably, the reaction with oxalyl chloride is run in a non-polar aprotic solvent, more preferably dichloromethane. Preferably, the reaction with the amine is run in a non-polar solvent, more preferably THF.

Synthetic examples of the production of isotopically labeled benzyl pyruvate and isotopically labeled pyruvic acid are as follows:

Step 1: Synthesis of [1-$^{13}$C]Methacrylic Acid.

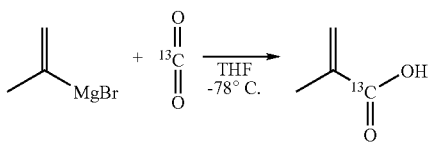

An oven dried 2 L 3-neck round bottom flask equipped with a 300 mm Allihn reflux condenser with gas adapter, heating mantle, 125 mL addition funnel with septa, and mechanical stirrer was placed under vacuum and back filled with Argon. Isopropenyl magnesium bromide (0.6 moles) was then added to the round-bottom flask, and cooled and maintained at – keep with 78 C with a dry ice/acetone bath. The $^{13}$CO$_2$ was bubbled into the Grignard via a needle and measured with a flow meter set at about 200 mL per minute, 27 g, 0.6 moles. The addition took about 55 minutes. After addition, the reaction was stirred for fifteen minutes. Meanwhile, 100 mL of concentrated 12M HCl, 1.2 moles, was diluted with 100 mL of water and transferred to the addition funnel in portions and added as a steady stream to the Grignard over about ten minutes. After addition, the cold bath was removed and replaced with water, to warm the reaction to room temperature. The resulting mostly colorless biphasic mixture was transferred to a 2L separatory funnel. The lower aqueous phase was made acidic by addition of 0.6 moles of HCl. The aqueous was extracted with dichloromethane (3×200 mL) and was separated. The organic layers were combined and washed with 0.7 moles. of NaOH. The aqueous layer was separated and evaporated to dryness. The [1-$^{13}$C] sodium methacylate was used in the subsequent reaction without purification.

Step 2: Synthesis of Benzyl [1-$^{13}$C]Methacrolate.

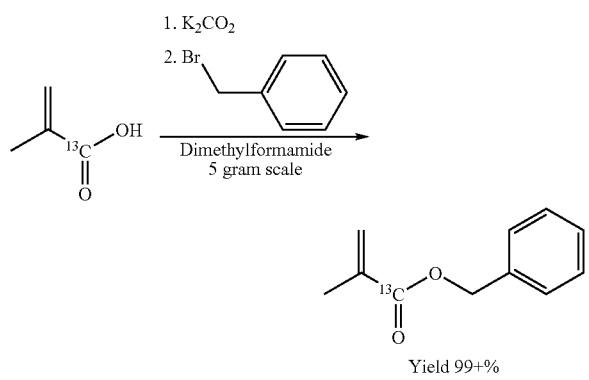

The [1-$^{13}$C]sodium methacylate was added to dimethyl formamide (DMF) (250 mL) in a 2 L round bottom flask at room temperature. This mixture was allowed to stir for about five minutes and then benzyl chloride (77.195 g, 0.6098 mol, 70.18 mL) was added at a quick drip rate over a twelve minute period. The reaction proceeded for six hours. Dichloromethane (750 mL) was added to the mixture and this mixture was filtered through a frit funnel. It was then transferred to a separatory funnel and was washed with DI water (3×150 mL). The last wash (4th) was done using sodium thiosulfate (15 g in 150 mL) to remove iodine from the solution. The organic extract was dried over sodium sulfate and evaporated in vacuo to a slightly yellow oil containing the desired product with some DMF. The DMF was removed under vacuum by heating the flask to 40° C. until about all of the DMF solvent was removed.

Step 3: Synthesis of Benzyl [1-13C]Pyruvate

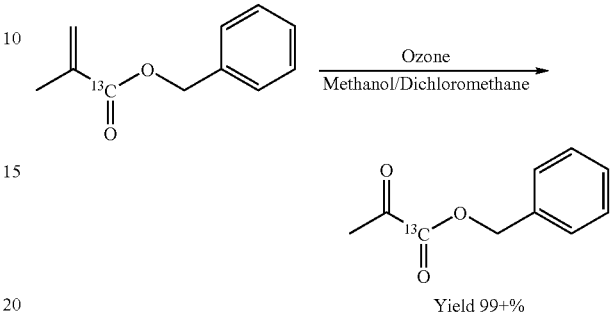

A stirred solution of 25 mL (147.5 mmole) of benzyl methacrylate in 500 mL of dichloromethane and 125 mL of methanol was cooled to −78° C. and ozonized until the solution was pale blue, indicating excess ozone. The solution was purged with nitrogen until the blue color of ozone had dissipated, and then 14.1 mL (192 mmole, 1.3 equivalents) of dimethyl sulfide was added rapidly dropwise under nitrogen. After stirring for one hour more at −78° C. the solution was removed from the cold bath and allowed to stir at room temperature for 3 hours. The solution may be stored overnight in the freezer at this point. Volatiles were removed on the rotary evaporator at 40° C. and the residue was taken up in 100 mL of dichloromethane and washed with 100 mL of water to remove dimethyl sulfoxide. The water layer was back extracted with a small volume of dichloromethane. The combined organics were washed with water in this fashion twice more. The final organic layer was filtered through cotton, concentrated on the rotary evaporator, and high-vacuum dried leaving an essentially quantitative yield of benzyl pyruvate as a colorless liquid. A small amount of formaldehyde methyl hemiacetal and/or the methyl hemiacetal of benzyl pyruvate may be present but do not interfere in the next step.

Step 4: Synthesis of [1-13C]Pyruvic Acid

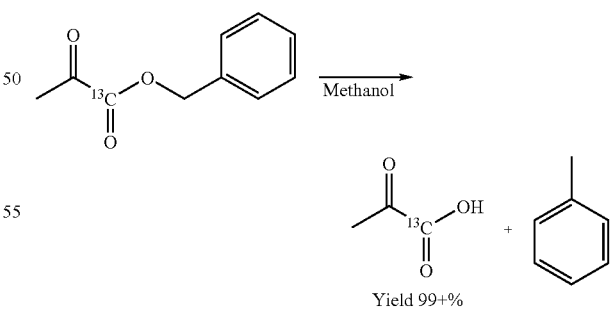

5 g (28 mmole) of the above benzyl pyruvate was dissolved in 100 mL of absolute ethanol in a heavy-walled bottle and blanketed with nitrogen. 0.5 g of 5% palladium on charcoal catalyst was added and the mixture was in a Parr shaker hydrogenation apparatus. The mixture was deaerated three times by evacuation followed by refilling with hydrogen. Hydrogenation was then commenced at 8 psi for one hour.

Hydrogen was then removed by evacuation followed by refilling with nitrogen. Catalyst was removed by vacuum filtration through a bed of Celite. The filter cake was washed with ethanol and the colorless to pale yellow filtrate was concentrated on the rotary evaporator at room temperature. Excessive vacuum or higher temperature must be avoided to prevent loss of product. The product obtained still contained a little ethanol and showed pyruvic acid, varying amounts of its ethyl hemiacetal, and a very small amount of ethyl pyruvate by NMR. Water may be added and distilled off at a bath temperature of less than 50° C. under high vacuum with liquid nitrogen cooling of the receiver. After most of the water was removed, additional water was added to the pot and the process repeated. What remained was a concentrated solution of pyruvic acid and its hydrate possibly contaminated by a little formaldehyde hydrate and ethyl pyruvate. Titration with 1N aqueous sodium hydroxide to an endpoint of pH 5.8 and removal of water and other volatiles yielded solid sodium pyruvate.

The reaction above could also be run in other solvents for example the reaction was run using acetone and at the end of the process [1-13C]Pyruvic acid was isolated as a mixture of 2 parts pyruvic acid to 1 of acetone. For example, the Hydrogenation of benzyl [1-$^{13}$C]pyruvate using acetone is accomplished as follows: Benzyl [1-$^{13}$C]pyruvate (5.1 g, 0.0285 moles) was dissolved in acetone (51 mL) and placed in a hydrogenation vessel which had 10% Pd/carbon (0.28 g). The reaction was purged with argon and then the reaction was evacuated under vacuum. The reaction vessel was filled with hydrogen to 10 psi and then shaken for 24 hours. The reaction was filtered to remove the catalyst and then concentrated. This mixture, which now contained toluene and [1-$^{13}$C]pyruvic acid, was treated with hexane. The layers were then separated and the hexane layer which contained the [1-$^{13}$C]pyruvic acid was evaporated to give a quantitative yield of the desired product as a mixture of acetone to [1-$^{13}$C]pyruvic acid (1:2).

Shelf Stability of Isotopically Labeled Pyruvic Acid:

Samples of isotopically labeled [1-$^{13}$C] pyruvic acid, having Formula VI and synthesized as discussed immediately below, were subjected to various conditions as depicted in Table 1, in order to establish the compound's shelf storage stability.

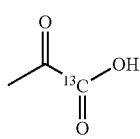

(Formula VI)

The [1-$^{13}$C] pyruvate of Formula VI was synthesized as follows:

Benzyl [1-$^{13}$C] pyruvate, Formula VIA, was synthesized according to the methods discussed previously. The benzyl [1-$^{13}$C] pyruvate was hydrogenated and the hydrogenation mixture was diluted with water and then extracted with dichloromethane. The organic phase contained toluene and some methanol while the aqueous phase contained the [1-$^{13}$C] pyruvic acid and methanol. The aqueous phase was then distilled until all of the methanol was removed, thereby leaving [1-$^{13}$C] pyruvic acid (purity: 98+/−2%, by NMR).

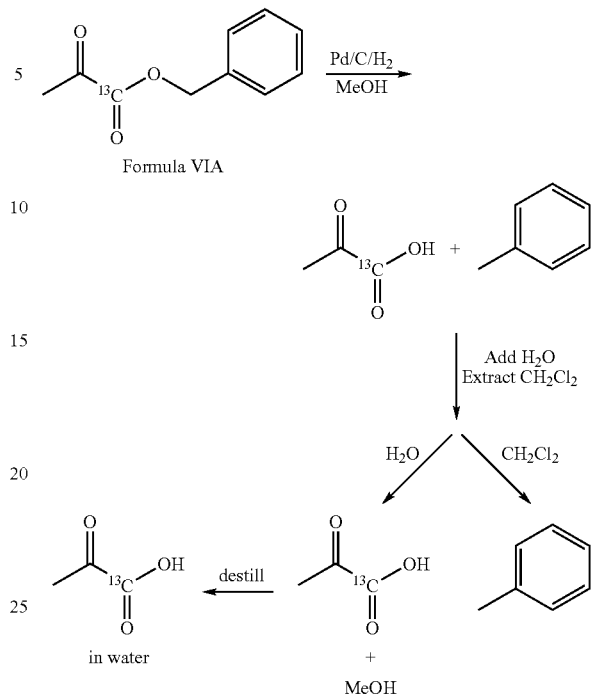

The resulting [1-$^{13}$C] pyruvic acid was tested as follows in Table 1:

TABLE 1

Samples of isotopically labeled pyruvic acid were subjected to various storage conditions.

| | Condition | | Duration | |
|---|---|---|---|---|
| Sample | Temperature | Storage | 12 weeks | 17 weeks |
| 1 | −10° C. | Dark | Stable | Stable |
| 2 | 4° C. | Dark | Stable | Stable |
| 3 | Room temperature* | Dark | Stable | Stable |
| 4 | Room temperature* | Light | Stable | Stable |

*Room temperature denotes a temperature ranging from about 22° C. to about 26° C.

$^1$H and $^{13}$C NMR spectra of the distilled [1-$^{13}$C] pyruvic acid in water (0.025M) were acquired at the onset of the study and prior to exposing the samples to the various conditions specified in Table 1. $^1$H and $^{13}$C NMR spectra were again acquired for each of the samples after being exposed to the aforementioned conditions on a weekly basis for 12-weeks. The spectra acquired after exposure were compared visually and appeared to remain unchanged as compared with the spectra acquired prior to exposure, i.e. the spectra were as expected for [1-$^{13}$C] pyruvic acid in water. As such, it was concluded that each of the samples were shelf stable. Similarly, $^1$H and $^{13}$C NMR spectra acquired after 17-weeks of exposure remained unchanged as compared with the spectra acquired prior to exposure. Once again, it was concluded that each of the samples were shelf stable under the conditions provided in Table 1.

Concentration studies were also performed to show that [1-$^{13}$C] pyruvic acid solutions would also be expected to be stable at higher concentrations. To demonstrate such stability, the [1-$^{13}$C] pyruvic acid solutions were compared to commercial samples of pyruvic acid (Formula VIB) obtained from Sigma-Aldrich Co. in water at higher concentrations. Commercial pyruvic acid was dissolved in water to arrive at the various concentrations listed in Table 2 below. Each of these commercial solutions were subjected to light for 6-weeks at temperatures ranging from about 22° C. to about 26° C. At each of the concentrations listed below, it was discovered that the pyruvic acid solutions were stable. As the purity of the commercial pyruvic acid samples were comparable to the purity of the materials produced in accordance with the present invention, and as the commercial materials were stable in water for at least 6 weeks at relatively high concentrations, it is believed that [1-$^{13}$C] pyruvic acid solutions having at least those concentrations in water would also be stable.

TABLE 2

Pyruvic acid, of varying concentrations, was found to be stable after 6-weeks.

(Formula VIB)

| Concentration | After 6-weeks |
|---|---|
| 11.3 | Stable |
| 5.7 | Stable |
| 3.8 | Stable |
| 2.8 | Stable |
| 2.3 | Stable |

The molarity of sample 4 was confirmed to be 0.025M by titrating the aqueous sample with sodium hydroxide. The titration with the sodium hydroxide also revealed that in acidic conditions, such as at pHs ranging from about 5.8 to about 1, pyruvic acid may be present either as the acid or as sodium [1-$^{13}$C] pyruvate, depending on the sodium hydroxide concentration. It was also discovered that at pHs greater than 5.8, such as at a pH of about 6.2, some of the pyruvic acid was present in the form of a dimerized sodium salt. For example, at a pH of about 6.2, the pH attained in titrating the solution of sample 4, HPLC revealed that sample 4 consisted of 89% sodium [1-$^{13}$C] pyruvate and about 2-4% dimerized [1-$^{13}$C] pyruvate salt (accounting for about 4-6% of the pyruvic acid). As such, it was discovered that to minimize dimmer formation, it may be necessary to control the pH of [1-$^{13}$C] pyruvate solutions, and in particular, any aqueous solution should be maintained at a pH of about 6.5 or less, more preferably 6.0 or less, and even more preferably 5.8 or less.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A process of forming an isotopically labeled compound of Formula (IIIb)

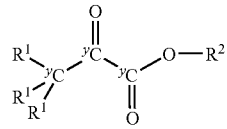

(Formula (IIIb))

comprising reacting a compound having Formula (IIIa)

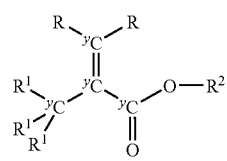

(Formula (IIIa))

with ozone in a solvent, wherein said solvent is selected from the group consisting of a $C_1$-$C_6$ alcohol, methylene chloride, and chloroform;

wherein
$R^2$ is —$CH_2$—$R^4$;
$R^4$ is selected from the group consisting of phenyl, naphthyl, benzofuran, isobenzofuran, indole, benzothiophene, benzimidazole, indazole, benzoxazole, benzisoxazole, benzothiazole, pyridine, quinoline, isoquinoline, pyrazine, quinoxaline, pyridazine, cinnoline and the substituted variants thereof;
each R and each $R^1$ are independently selected from the group consisting of hydrogen, deuterium, and a $C_1$-$C_4$ straight chain or branched alkyl;
each $^yC$ is selected from the group consisting of $^{12}C$; $^{13}C$ or $^{14}C$ and at least one of said $^yC$ is selected from the group consisting of $^{13}C$ or $^{14}C$,
wherein the isotopically labeled compound of Formula (IIIb) is isotopically enriched.

2. The process of claim 1, wherein all R and all $R^1$ groups are hydrogen; and $R^2$ is benzyl.

3. The process of claim 1, wherein said reaction is run at a temperature at about 0° C. and below.

* * * * *